(12) United States Patent
Rolf et al.

(10) Patent No.: US 10,219,880 B2
(45) Date of Patent: Mar. 5, 2019

(54) DENTAL MILL BLANK

(71) Applicant: 3M INNOVATIVE PROPERTIES COMPANY, St. Paul, MN (US)

(72) Inventors: Jacqueline C. Rolf, River Falls, WI (US); Richard P. Rusin, Woodbury, MN (US); Colin F. Norman, Hudson, WI (US); Melinda B. Gustafson, Lake Elmo, MN (US); James D. Hamer, White Bear Lake, MN (US); Charles G. Carter, Woodbury, MN (US); Roxanne A. Boehmer, Inver Grove Heights, MN (US); Brian N. Holmes, St. Paul, MN (US); Tara Waldrop, Los Alamos, NM (US); Brady P. Haislet, Maple Plain, MN (US)

(73) Assignee: 3M Innovative Properties Company, St, MN (US)

( * ) Notice: Subject to any disclaimer, the term of this patent is extended or adjusted under 35 U.S.C. 154(b) by 75 days.

(21) Appl. No.: 15/026,293

(22) PCT Filed: Oct. 2, 2014

(86) PCT No.: PCT/US2014/058787
§ 371 (c)(1),
(2) Date: Mar. 31, 2016

(87) PCT Pub. No.: WO2015/051095
PCT Pub. Date: Apr. 9, 2015

(65) Prior Publication Data
US 2016/0228222 A1    Aug. 11, 2016

Related U.S. Application Data

(60) Provisional application No. 61/887,194, filed on Oct. 4, 2013.

(51) Int. Cl.
*A61C 13/09* (2006.01)
*A61C 13/00* (2006.01)
*A61C 13/08* (2006.01)

(52) U.S. Cl.
CPC ...... *A61C 13/0022* (2013.01); *A61C 13/0004* (2013.01); *A61C 13/0006* (2013.01); *A61C 13/082* (2013.01); *A61C 13/09* (2013.01)

(58) Field of Classification Search
None
See application file for complete search history.

(56) References Cited

U.S. PATENT DOCUMENTS

| | | |
|---|---|---|
| 3,066,112 A | 11/1962 | Bowen |
| 3,117,099 A | 1/1964 | Proops |

(Continued)

FOREIGN PATENT DOCUMENTS

| | | |
|---|---|---|
| DE | 19944130 | 4/2001 |
| EP | 0173567 | 3/1986 |

(Continued)

OTHER PUBLICATIONS

Machine translation of EP 0850601 dated Aug. 15, 2017.*
International Search Report for PCT International Application No. PCT/US2014/058787 dated Jan. 7, 2015, 6 pages.

*Primary Examiner* — Daniel J. Schleis

(57) ABSTRACT

Disclosed herein a dental mill blank and a method of forming the dental mill blank. The dental mill blank includes a first layer of a first hard restorative material having a first translucency and a first shade, a second layer of a second hard restorative material having a second translucency and a second shade, where at least one of the following is true (1) the first translucency is different from the second translucency, (2) the first shade is different from the second shade. The first layer and the second layer form a first interface having a first curve across a first plane of symmetry (Continued)

of the dental mill blank, where the first curve has a different from zero curvature; and a first straight line along the entire length of a second plane of the dental mill blank, the second plane being orthogonal to the first plane of symmetry.

21 Claims, 8 Drawing Sheets

(56) References Cited

U.S. PATENT DOCUMENTS

| | | |
|---|---|---|
| 3,539,533 A | 11/1970 | Lee |
| 3,629,187 A | 12/1971 | Waller |
| 3,708,296 A | 1/1973 | Schlesinger |
| 3,709,866 A | 1/1973 | Waller |
| 3,751,399 A | 8/1973 | Lee |
| 3,766,132 A | 10/1973 | Lee |
| 3,860,556 A | 1/1975 | Taylor |
| 4,002,669 A | 1/1977 | Gross |
| 4,069,055 A | 1/1978 | Crivello |
| 4,115,346 A | 9/1978 | Gross |
| 4,216,288 A | 8/1980 | Crivello |
| 4,250,311 A | 2/1981 | Crivello |
| 4,259,117 A | 3/1981 | Yamauchi |
| 4,292,029 A | 9/1981 | Craig |
| 4,298,738 A | 11/1981 | Lechtken |
| 4,308,190 A | 12/1981 | Walkowiak |
| 4,324,744 A | 4/1982 | Lechtken |
| 4,327,014 A | 4/1982 | Kawahara |
| 4,356,296 A | 10/1982 | Griffith |
| 4,379,695 A | 4/1983 | Orlowski |
| 4,385,109 A | 5/1983 | Lechtken |
| 4,387,240 A | 6/1983 | Berg |
| 4,404,150 A | 9/1983 | Tsunekawa |
| 4,503,169 A | 3/1985 | Randklev |
| 4,575,805 A | 3/1986 | Moermann |
| 4,642,126 A | 2/1987 | Zador |
| 4,648,843 A | 3/1987 | Mitra |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,772,436 A | 9/1988 | Tyszblat |
| 4,837,732 A | 6/1989 | Brandestini |
| 4,910,032 A | 3/1990 | Antoon, Jr. |
| 4,957,554 A | 9/1990 | Mathers |
| 4,970,032 A | 11/1990 | Rotsaert |
| 4,985,340 A | 1/1991 | Palazzotto |
| 5,026,902 A | 6/1991 | Fock |
| 5,076,844 A | 12/1991 | Fock |
| 5,084,586 A | 1/1992 | Farooq |
| 5,089,536 A | 2/1992 | Palazzotto |
| 5,124,417 A | 6/1992 | Farooq |
| 5,151,044 A | 9/1992 | Rotsaert |
| 5,545,676 A | 8/1996 | Palazzotto |
| 5,591,030 A | 1/1997 | Thiel |
| 5,843,348 A | 12/1998 | Giordano |
| 5,856,373 A | 1/1999 | Kaisaki |
| 5,869,548 A | 2/1999 | Ikushima |
| 5,910,273 A | 6/1999 | Thiel |
| 5,990,195 A | 11/1999 | Arita |
| 5,998,549 A | 12/1999 | Milbourn |
| 6,025,406 A | 2/2000 | Oxman |
| 6,030,606 A | 2/2000 | Holmes |
| 6,159,417 A | 12/2000 | Giordano |
| 6,251,963 B1 | 6/2001 | Kohler |
| 6,271,282 B1 | 8/2001 | Giordano |
| 6,306,926 B1 | 10/2001 | Bretscher |
| 6,342,458 B1 | 1/2002 | Schweiger |
| 6,345,984 B2 | 2/2002 | Karmaker |
| 6,375,729 B1 | 4/2002 | Brodkin |
| 6,376,590 B2 | 4/2002 | Kolb |
| 6,379,593 B1 | 4/2002 | Datzmann |
| 6,387,981 B1 | 5/2002 | Zhang |
| 6,488,503 B1 | 12/2002 | Lichkus |
| 6,572,693 B1 | 6/2003 | Wu |
| 6,713,421 B1 | 3/2004 | Hauptmann |
| 6,730,156 B1 | 5/2004 | Windisch |
| 6,765,036 B2 | 7/2004 | Dede |
| 6,818,682 B2 | 11/2004 | Falsafi |
| 6,846,181 B2 | 1/2005 | Karmaker |
| 6,878,456 B2 | 4/2005 | Castro |
| 6,881,488 B2 | 4/2005 | Giordano |
| 6,899,948 B2 | 5/2005 | Zhang |
| 6,984,261 B2 | 1/2006 | Cummings |
| 7,022,173 B2 | 4/2006 | Cummings |
| 7,030,049 B2 | 4/2006 | Rusin |
| 7,085,063 B2 | 8/2006 | Magarill |
| 7,090,721 B2 | 8/2006 | Craig |
| 7,090,722 B2 | 8/2006 | Budd |
| 7,156,911 B2 | 1/2007 | Kangas |
| 7,160,528 B2 | 1/2007 | Rusin |
| 7,294,392 B2 | 11/2007 | Aechtner |
| 7,361,216 B2 | 4/2008 | Kangas |
| 7,393,882 B2 | 7/2008 | Wu |
| 7,429,422 B2 | 9/2008 | Davidson |
| 7,649,029 B2 | 1/2010 | Kolb |
| 7,807,227 B2 | 10/2010 | Aechtner |
| 7,845,947 B2 | 12/2010 | Rusin |
| 7,892,995 B2 | 2/2011 | Castillo |
| 7,981,531 B2 | 7/2011 | Rheinberger |
| 7,993,137 B2 | 8/2011 | Apel |
| 8,025,992 B2 * | 9/2011 | Engels ............... A61C 13/0022 428/701 |
| 8,133,828 B2 | 3/2012 | Denry |
| 8,309,015 B2 | 11/2012 | Rolf |
| 8,507,578 B2 | 8/2013 | Sadoun |
| 8,536,078 B2 | 9/2013 | Ritzberger |
| 2004/0024470 A1 | 2/2004 | Giordano |
| 2004/0081847 A1 | 4/2004 | Aechtner |
| 2005/0127544 A1 | 6/2005 | Brodkin |
| 2009/0220917 A1 | 9/2009 | Jensen |
| 2009/0220918 A1 | 9/2009 | Kaufmann |
| 2010/0089286 A1 | 4/2010 | Craig |
| 2010/0285429 A1 | 11/2010 | Karim |
| 2011/0104643 A1 | 5/2011 | Giordano |
| 2011/0189636 A1 * | 8/2011 | Thiel ................ A61C 13/0022 433/199.1 |
| 2011/0196062 A1 | 8/2011 | Craig |
| 2011/0236855 A1 | 9/2011 | Rheinberger |
| 2011/0236857 A1 | 9/2011 | Rheinberger |
| 2011/0257000 A1 | 10/2011 | Ritzberger |
| 2012/0248657 A1 | 10/2012 | Elbert |
| 2013/0115364 A1 | 5/2013 | Zandinejad |
| 2013/0172441 A1 | 7/2013 | Takahata |

FOREIGN PATENT DOCUMENTS

| | | | |
|---|---|---|---|
| EP | 0850601 | * 3/2005 | ............... A61C 5/08 |
| EP | 0850601 | 8/2009 | |
| GB | 2291053 | 1/1996 | |
| WO | WO 2000-38619 | 7/2000 | |
| WO | WO 2000-42092 | 7/2000 | |
| WO | WO 2001-07444 | 2/2001 | |
| WO | WO 2001-92271 | 12/2001 | |
| WO | WO 2002-09612 | 2/2002 | |
| WO | WO 2003-063804 | 8/2003 | |
| WO | WO 2011-087832 | 7/2011 | |
| WO | WO 2013-060460 | 5/2013 | |
| WO | WO 2014-062375 | 4/2014 | |

* cited by examiner

DENTAL MILL BLANK

FIELD OF DISCLOSURE

The disclosure relates to dental mill blanks and in particular dental mill blanks for producing dental restoration.

BACKGROUND

Dental mill blanks are blocks of material from which dental restorations are formed. Dental mill blanks come in a variety of shades and translucencies. The dental professional selects the shade and translucency of the dental mill blank for the dental restoration in an effort to best match the natural shade and translucency of the patient's natural dental anatomy. These natural dental anatomies, however, have a variety of shades and translucencies that are very difficult to capture.

This difficulty arises because natural dental anatomies (e.g., natural teeth) have a gradient of shades and translucencies extending from the gingival region to the incisal edge/occlusal surface due to the internal structure of the teeth. In an attempt to mimic this gradient, dental mill blanks have been formed with multiple flat planar layers, where each layer has at least one different shade and/or translucency. Unfortunately, dental restorations formed from these dental mill blanks have transitions between the flat planar layers that are perceived to be unnatural. Other attempts to mimic the gradient include dental mill blanks that have a discrete shape of material with one shade and/or translucency and a surrounding layer with another shade and/or translucency. Examples of such dental mill blanks include VITABLOCS® RealLife® (Vita Zahnfabrik H. Rauter GmbH & Co., Bad Säckingen, Germany; or CEREC® Blocks C In (Sirona Dental Technologies, Bensheim, Germany)). Forming dental restorations from these dental mill blanks is, however, difficult because they require precise positioning of the restoration design within the dental mill blanks during milling in order to achieve a desired aesthetic result.

As such, there is a need in the art for dental mill blanks that allow for both simple positioning of the restoration design for milling and that will produce a dental restoration with a gradient of shades and translucencies having a natural appearance.

SUMMARY

The present disclosure provides a dental mill blank that both allows for simple positioning of the restoration design in dental mill blank for milling and that will produce a dental restoration with a gradient of shades and translucencies having a natural appearance so as to blend better with the adjacent natural dentition. The dental mill blank of the present disclosure also allows for its production in a highly cost effective matter while still allowing for a dental restoration produced therefrom that has a natural appearance. These and other aspects of the dental mill blank of the present disclosure will be discussed more fully herein.

The dental mill blank of the present disclosure includes a first layer of a first hard restorative material having a first translucency and a first shade; a second layer of a second hard restorative material having a second translucency and a second shade, where at least one of the following is true: the first translucency is different from the second translucency and/or the first shade is different from the second shade. The first layer and the second layer form a first interface having a first curve across a first plane of symmetry of the dental mill blank, where the first curve has a different from zero curvature; and a first straight line along the entire length of a second plane of the dental mill blank, the second plane being orthogonal to the first plane of symmetry.

The curve of the dental mill blank can be a smooth curve. The smooth curve can be selected from the group consisting of a circle, a semi-circle, a circular arc, an ellipse, an ellipsoidal arc, a parabola, an oval, a semi-oval, an ovoid arc or a catenary. So, for example, the first layer of the first hard restorative material can have a negative curvature and the second layer of the second hard restorative material can have a positive curvature. In one embodiment, the first hard restorative material and the second hard restorative material are not physically blended at the first interface.

In an embodiment, the first translucency of the first hard restorative material is greater than the second translucency of the second hard restorative material. For this given configuration of translucency, it is possible that the first shade and the second shade can be equal, or, in another embodiment, the first shade can be different from the second shade. For example, the first translucency of the first hard restorative material can be greater than the second translucency of the second hard restorative material, and the first shade of the first hard restorative material can be lighter than the second shade of the second hard restorative material.

The dental mill blank can further include a third layer of a third hard restorative material, where the third layer and the second layer form a second interface. The third hard restorative material can have a third translucency and a third shade, where at least one of the following is true: the second translucency is different from the third translucency; and the second shade is different from the third shade. The second layer and the third layer form a second interface having a second curve across the first plane of symmetry of the dental mill blank, where the second curve has a different from zero curvature; and a second straight line along the entire length of a second plane of the dental mill blank, the second plane being orthogonal to the first plane of symmetry.

A dental restoration can be shaped from the dental mill blank of the present disclosure.

The present disclosure further includes a method of forming a dental mill blank that includes joining a first layer of a first restorative material and a second layer of a second restorative material to form the first interface having the first curve across the first plane of symmetry of the dental mill blank, and the first straight line along the entire length of a second plane of the dental mill blank; and hardening the first restorative material and the second restorative material to form the first hard restorative material and the second hard restorative material. Joining the first layer of the first restorative material and the second layer of the second hard restorative material can form the smooth curve for the first interface.

The method can further include joining a third layer of a third restorative material with the second layer of the second restorative material, where the second layer and the third layer form the second interface have the second curve across the first plane of symmetry of the dental mill blank, and the second straight line across the entire length of the second plane of the dental mill blank; and hardening the third restorative material along with the first restorative material and the second restorative material to form the first hard restorative material, the second hard restorative material and a third hard restorative material of the dental mill blank.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The drawings may not be to scale.

Definitions

Figure 1:
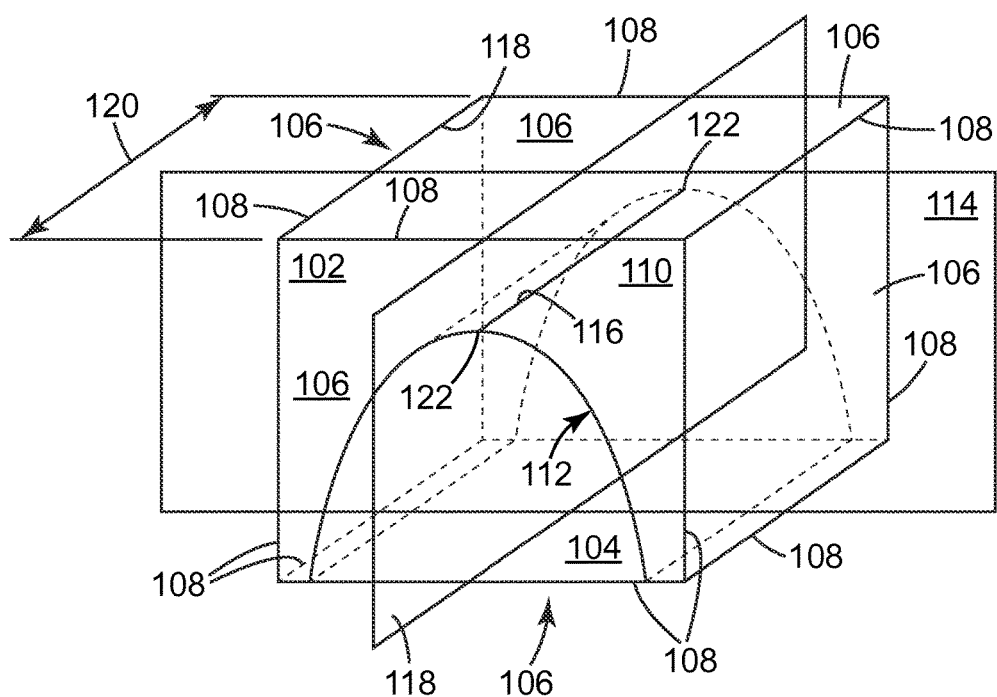
FIG. 1 is a perspective view of a dental mill blank according to an embodiment of the present disclosure.

As used herein, "a," "an," "the," "at least one," and "one or more" are used interchangeably. The term "and/or" means one, one or more, or all of the listed items. The recitations of numerical ranges by endpoints include all numbers subsumed within that range (e.g., 1 to 5 includes 1, 1.5, 2, 2.75, 3, 3.80, 4, 5, etc.).

As used herein a "hard restorative material" is a restorative material that has undergone a physical and/or a chemical transformation to produce a solid and firm restorative material that is resistant to pressure. The physical and/or chemical transformation of the restorative material can be due to a setting, curing, polymerizing, firing, crosslinking, fusing or a sintering process.

As used herein, "equal" means that for a given property, measurements of that property are the same in quantity, size, degree or value. So, for example, when a first hard restorative material has a first shade value of "A1" and a second hard restorative material has a second shade value of "A1", the first shade and the second shade are "equal."

As used herein a "shade" is a color as defined by the "CIE 1976 (L*, a*, b*) color space, generally referred to as CIELAB.

As used herein "translucency" is the degree to which a material transmits light. This may be quantified by contrast ratio, translucency parameter, or percent transmittance through a known thickness of material. Translucency in dental materials is often determined from the contrast ratio. The contrast ratio is the ratio of white light remission from a specimen placed over a standardized black background (Yb) and a standardized white background (Yw). The contrast ratio is calculated as CR=Yb/Yw. A contrast ratio of 1 represents a completely opaque specimen. Translucency is expressed as 1-CR.

As used herein a "curve" is a line (e.g., formed by an interface between layers of the hard restorative material) that deviates from being straight (e.g., has a different from zero curvature) for some or all of its length. Examples of different from zero curvature for the line forming the curve include a greater than zero curvature or a less than zero curvature.

As used herein an "interface" is a surface forming a common boundary between adjacent layers of restorative material, including hard restorative material.

As used herein a "dental mill blank" is a block of material (e.g., hard restorative material) from which dental restorations can be milled.

The term "dental restoration" means a replacement for tooth structure. Examples include restoratives, replacements, inlays, onlays, veneers, full crowns, partial crowns, bridges, dentures, implants, implant abutments, implant healing caps, posts, temporary restorations, and the like. In this respect, the dental restoration shall have sufficient strength.

By "machining" is meant milling, grinding, cutting, carving, or shaping a material having a three dimensional structure or shape by a machine.

A "hardenable compound" is a compound which can be cured, polymerized or solidified e.g. by chemical crosslinking through radiation-induced polymerization, crosslinking, sintering, firing, fusing, heating or by using an initiator.

A "composite" is a hardenable (or hardened) composition containing at least in part, a polymerizable (or polymerized) resin(s), filler particles of one or more types, one or more polymerization initiators, and any desired adjuvants.

By "nanofiller" is meant a filler having an average primary particle size of at most 200 nanometers. The nanofiller component may be a single nanofiller or a combination of nanofillers. For certain embodiments, the nanofiller comprises non-pyrogenic nanoparticles or nanoclusters.

By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" "nanosized particles," refer to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are discrete, non-aggregated and non-agglomerate particles.

By "nanocluster" is meant an association of nanoparticles drawn together by relatively weak intermolecular forces that cause them to clump together, i.e. to aggregate. Typically, nanoclusters have an average size of at most 10 micrometers.

The term "comprising" and variations thereof (e.g., comprises, includes, etc.) do not have a limiting meaning where these terms appear in the description and claims.

As used herein, "CAD/CAM" is the abbreviation for computer-aided design/computer-aided manufacturing.

As used herein "lighter" means a hard restorative material having a shade that is closer to white (L*a*b*=100,0,0) or further from black ((L*a*b*=0,0,0) relative another hard restorative material. So, for example, a first hard restorative material that is "lighter" than a second hard restorative material is one in which the L* value of the first hard restorative material is greater than the L* value of the second hard restorative material.

As used herein "darker" means a hard restorative material having a shade that is closer to black (L*a*b*=0,0,0) or further from white ((L*a*b*=100,0,0) relative another hard restorative material. So, for example, a second hard restorative material that is "darker" than a first hard restorative material is one in which the L* value of the second hard restorative material is less than the L* value of the first hard restorative material.

DETAILED DESCRIPTION

The present disclosure is directed to a dental mill blank and a method of producing the dental mill blank, where the dental mill blank both allows for simple positioning of the restoration design in the dental mill blank for milling and that will produce a dental restoration with a gradient of shades and translucencies having a natural appearance so as to blend better with the adjacent natural dentition. The dental mill blank of the present disclosure also allows for its production in a highly cost effective matter while still allowing for a dental restoration produced therefrom that has a natural appearance.

In the following detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. For example, 214 may reference element "14" in FIG. 2, and a similar element may be referenced as 314 in FIG. 3. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense.

FIG. 1 provides a perspective view of a dental mill blank 100 according to one embodiment of the present disclosure. The dental mill blank 100 includes a first layer 102 of a first hard restorative material and a second layer 104 of a second hard restorative material. The dental mill blank 100 can be a cuboid having six quadrilateral faces 106 that define edges 108. Faces 106 opposite each other on the dental mill blank 100 can have the same shape and area. Examples of such cuboid structures include, but are not limited to, a cube (each of the six faces 106 are a square), a rectangular cuboid (each of the six faces 106 are a rectangle), a tetragonal prism (e.g., four of the faces 106 are rectangular and two of the faces 106 are square). Other shapes for the dental mill blank 100 are possible, as will be discussed herein.

As illustrated, the first layer 102 and the second layer 104 form a first interface 110 (shown with shading) that forms a first curve 112 across a first plane of symmetry 114 of the dental mill blank 100. As used herein, the first plane of symmetry 114 is an imaginary plane that bisects the dental mill blank 100 into two halves in which the first layer 102 and the second layer 104 are mirror images of each other. As illustrated, the first plane of symmetry 114 bisects the dental mill blank 100 orthogonal to four of the quadrilateral faces 106 and orthogonal to the first interface 110, as illustrated in FIG. 1.

The first curve 112 has a different from zero curvature. For example, the first curve 112 has a greater than zero curvature. The first curve 112 can be a variety of different curves. For example, the first curve 112 can be a smooth curve. Examples of such smooth curves include those selected from the group consisting of a circle, a semi-circle, a circular arc, an ellipse, an ellipsoidal arc, a parabola, an oval, a semi-oval, an ovoid arc or a catenary, as will be discussed and illustrated more fully herein. For these given shapes, the first layer 102 of the first hard restorative material can have a negative curvature, while the second layer 104 of the second hard restorative material has a positive curvature, as is illustrated in FIG. 1.

The dental mill blank 100 further includes a first straight line 116 formed by the first interface 112 taken along a second plane 118 that passes through both the first layer 102 and the second layer 104 of the dental mill blank 100, where the second plane 118 is orthogonal to the first plane of symmetry 114. As illustrated, the first straight line 116 extends along the entire length 120 of the dental mill blank 100. In addition, for a given position of the second plane 118, end points 122 of the first straight line 116 have the same relative position on the faces 106, opposite each other, on which they are present. The first straight line 116 can also maintain a parallel relationship with edges 108 that extend in a common direction (e.g., along the length 120 of the dental mill blank 100). As illustrated in FIG. 1, the second plane 118 can be a plane of symmetry for the dental mill blank 100 (e.g., bisects the dental mill blank 100 into two halves along the length 120, where the first layer 102 and the second layer 104 are mirror images of each other).

The first hard restorative material that forms the first layer 102 has a first translucency and a first shade. The second hard restorative material that forms the second layer 104 has a second translucency and a second shade. For this given combination of translucencies and shades at least one of the following is true: (1) the first translucency is different from the second translucency for equivalent thicknesses of the hard restorative material and (2) the first shade is different from the second shade. So, for example, the first translucency of the first hard restorative material that forms the first layer 102 can be greater (e.g., more translucent) than the second translucency of the second hard restorative material that forms the second layer 104, while the first shade of the first hard restorative material is equal to (e.g., the same as) the second shade of the second hard restorative material. It is also possible that the first shade of the first hard restorative material is lighter than the second shade of the second hard restorative material, while the first translucency and the second translucency are the same (e.g., equal). Finally, it is possible that the first translucency of the first hard restorative material is greater (e.g., more translucent) than the second translucency of the second hard restorative material and the first shade of the first hard restorative material is lighter than the second shade of the second hard restorative material.

For the various embodiments, the layers of the hard restorative material used in forming the dental mill blank of the present disclosure are not physically blended (e.g., not blended during their formation and/or hardening). In addition, no intermediate layers, as are known in the art, are applied between the layers of the hard restorative material used in forming the dental mill blanks of the present disclosure.

Referring now to FIGS. 2A through 2F, there are illustrated a variety of dental mill blanks 200 according to the present disclosure. Each of the dental mill blanks 200 is shown in a plane view, but it is understood that the geometry and the structures of the dental mill blank illustrated in FIG. 1 and discussed herein applies to the dental mill blanks 200. The dental mill blanks 200 includes the first layer 202 of the first hard restorative material and the second layer 204 of the second hard restorative material, as discussed herein. The dental mill blanks 200 also include the first curve 212, across the first plane of symmetry.

Figure 2A:
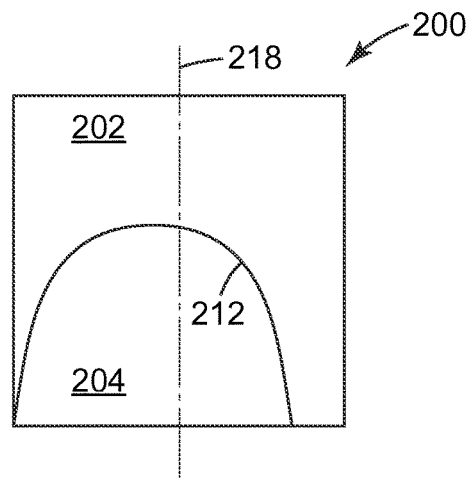
FIGS. 2A-2F are plane views of dental mill blanks according to various embodiments of the present disclosure.
Figure 2B:
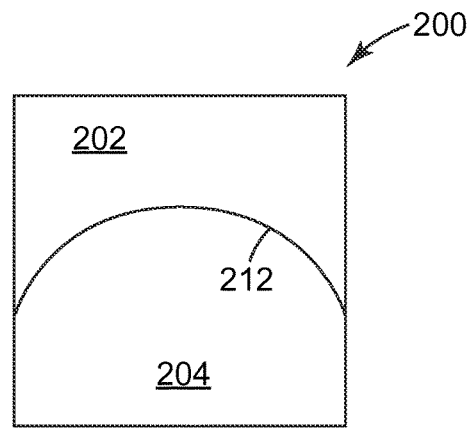
Figure 2C:
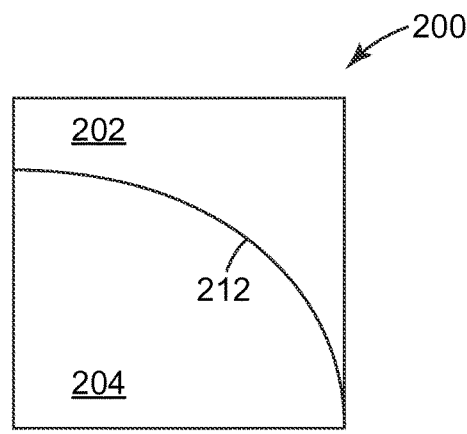
Figure 2D:
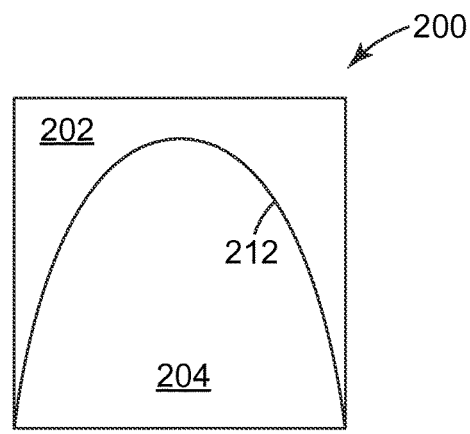
Figure 2E:
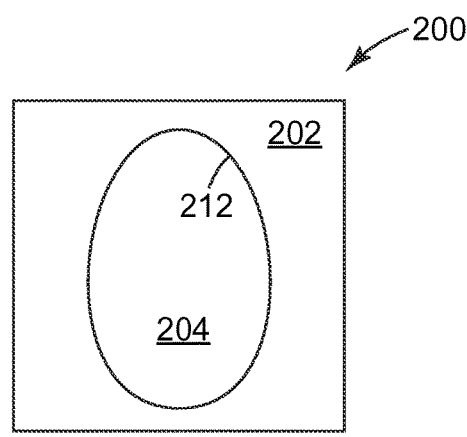
Figure 2F:
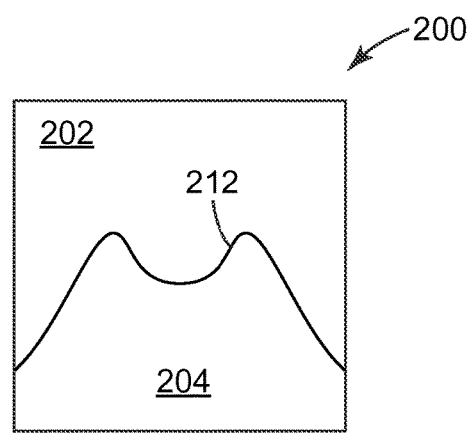

As illustrated in FIGS. 2A-2F, each of the first curves 212 has a different from zero curvature. FIG. 2A provides an example of the first curve 212 having a greater than zero curvature in a parabolic shape. FIG. 2A also provides an example where the vertex of the parabola formed by the first curve is not on the second plane 218 when it is along the axis of symmetry as shown in FIG. 2A. FIG. 2B provides an example of the first curve 212 having a semi-oval shape. FIG. 2C provides an example of the first curve 212 having a semi-circular shape. FIG. 2D provides an example of the first curve 212 having a catenary shape. FIG. 2E provides an example of the first curve 212 having an oval shape. Finally, FIG. 2F provides an example of the first curve 212 having a series of curved shapes (e.g., a series of parabolae). It is possible that a portion of the first curve 212 can be a straight line.

Figure 3:
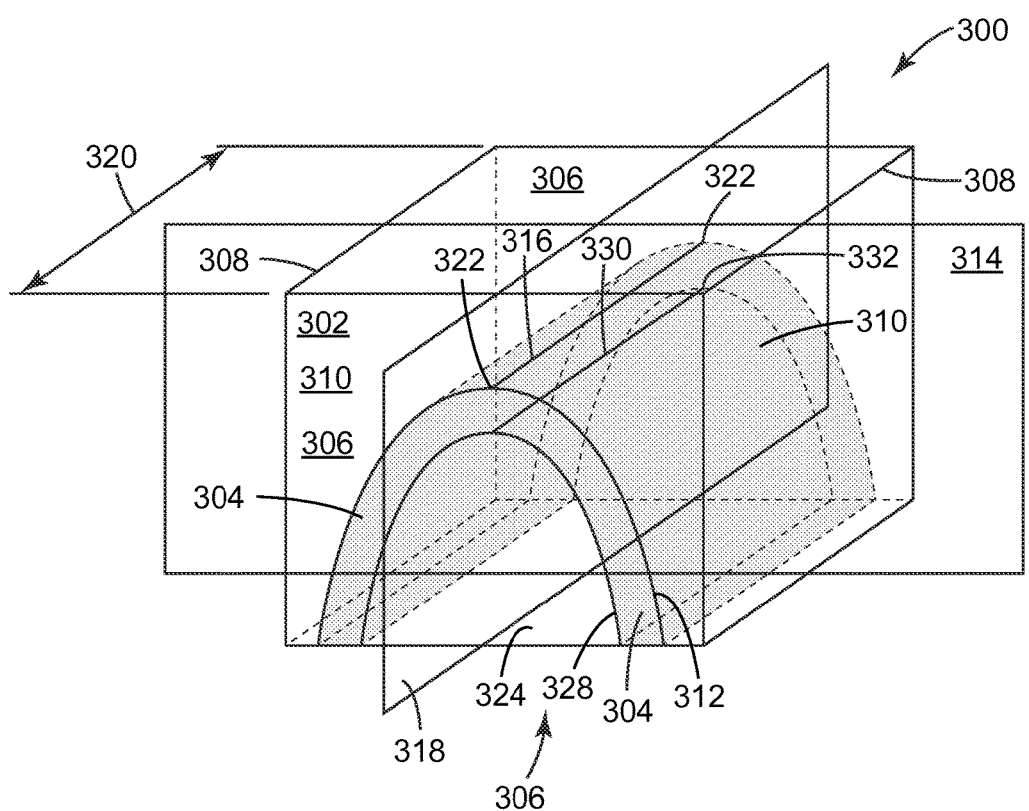
FIG. 3 is a perspective view of a dental mill blank according to an embodiment of the present disclosure.

Referring now to FIG. 3 there is shown an additional embodiment of the dental mill blank 300 of the present disclosure. The dental mill blank 300 includes the first layer 302 of a first hard restorative material and the second layer 304 of a second hard restorative material, as discussed herein. In addition, the dental mill blank 300 further includes a third layer 324 of a third hard restorative material, where the third layer 324 and the second layer 304 form a second interface 326. As illustrated, the second interface 326 has a second curve 328 across the first plane of symmetry 314 of the dental mill blank 300. The second curve 328 has a different from zero curvature.

Both the first curve 312 and the second curve 328 can have a variety of different curves. For example, both the first curve 312 and the second curve 328 can be a smooth curve, as discussed herein. For the various embodiments, the first curve 312 and the second curve 328 do not cross. For example, the first curve 312 and the second curve 328 can remain in the same relative position taken across the first plane of symmetry 314 along the entire length 320 of the dental mill blank 300. It is possible, however, that the first curve 312 and the second curve 328 may contact each other at one or more points across the first plane of symmetry 314 along the entire length 320 of the dental mill blank 300, as will be discussed more fully herein.

The dental mill blank 300 further includes both the first straight line 316, as discussed herein, and a second straight line 330 formed by the second interface 326 taken along the second plane 318 that passes through both the first layer 302 and the second layer 304 of the dental mill blank 300, where the second plane 318 is orthogonal to the first plane of symmetry 314, as discussed herein. As illustrated, the first straight line 316 and the second straight line 330 extend along the entire length 320 of the dental mill blank 300. In addition, for a given position of the second plane 318, end points 322 of the first straight line 316 and end points 332 of the second straight line 330 have the same relative position on the faces 306, opposite each other, on which they are present. The first straight line 316 and the second straight line 330 also maintain a parallel relationship each other and with the edges 308 that extend in a common direction (e.g., along the length 320 of the dental mill blank 300). As illustrated in FIG. 3, the second plane 318 can be a plane of symmetry for the dental mill blank 300 (e.g., bisects the dental mill blank 300 into two halves along the length 320), where the first layer 302 and the second layer 304 are mirror images of each other.

The third hard restorative material that forms the third layer 324 has a third translucency and a third shade. For the first hard restorative material, the second hard restorative material and the third restorative material can have a variety of combinations of translucencies and shades, where at least one of the following is true: the second translucency is different from the third translucency; and the second shade is different from the third shade.

So, for example, the first translucency of the first hard restorative material that forms the first layer 302 can be greater (e.g., more translucent) than the second translucency of the second hard restorative material that forms the second layer 304, and the second translucency of the second hard restorative material that forms the second layer 304 can be greater than the third translucency of the third hard restorative material that forms the third layer 324. For this embodiment, it is possible that the first shade of the first hard restorative material is equal to (e.g., the same as) at least one or both the second shade of the second hard restorative material and the third shade of the third hard restorative material. It is also possible that the second shade of the second hard restorative material is lighter than the third shade of the third hard restorative material and the first shade of the first hard restorative material is lighter than the second shade of the second hard restorative material.

In an additional example, the second shade of the second hard restorative material is lighter than the third shade of the third hard restorative material. For this embodiment, the first translucency can be equal to or greater than the second translucency and/or the third translucency, where the second translucency and the third translucency can be equal or the second translucency greater than the third translucency. In an additional embodiment, the first translucency can be greater than the second translucency, which is greater than the third translucency. Finally, it is possible that the first translucency of the first hard restorative material is greater (e.g., more translucent) than the second translucency of the second hard restorative, which has a translucency that is greater than the third translucency of the third hard restorative material, and the first shade of the first hard restorative material is lighter than the second shade of the second hard restorative material, which is lighter than the third shade of the third hard restorative material.

Referring now to FIGS. 4A through 4F, there are illustrated a variety of dental mill blanks 400 according to the present disclosure. Each of the dental mill blanks 400 is shown in a plane view, but it is understood that the geometry and the structures of the dental mill blank illustrated in FIG. 3 and discussed herein for both FIGS. 1 and 3 applies to the dental mill blanks 400. The dental mill blanks 400 includes the first layer 402 of the first hard restorative material, the second layer 404 of the second hard restorative material and third layer 424 of the third hard restorative material, as discussed herein. The dental mill blanks 400 also include the first curve 412 and the second curve 428, across the first plane of symmetry.

Figure 4A:
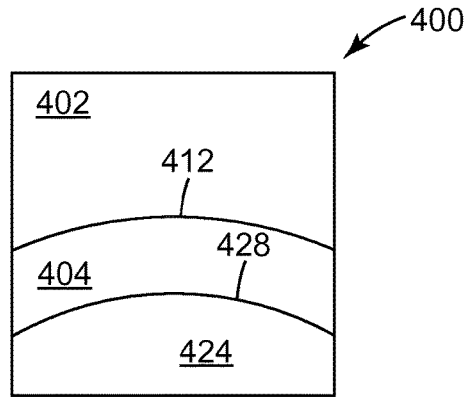
FIGS. 4A-4F are plane views of dental mill blanks according to various embodiments of the present disclosure.
Figure 4B:
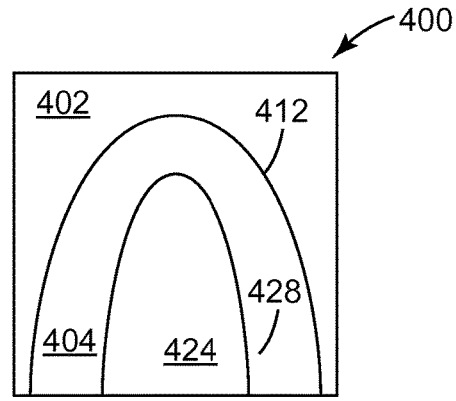
Figure 4C:
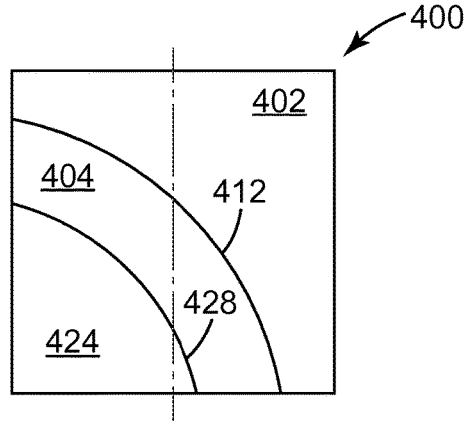
Figure 4D:
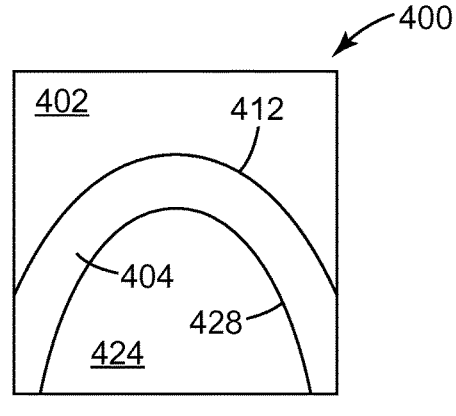
Figure 4E:
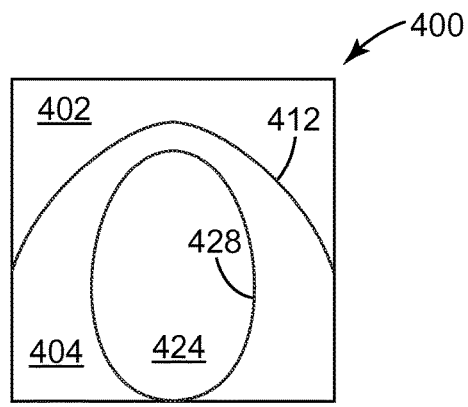
Figure 4F:
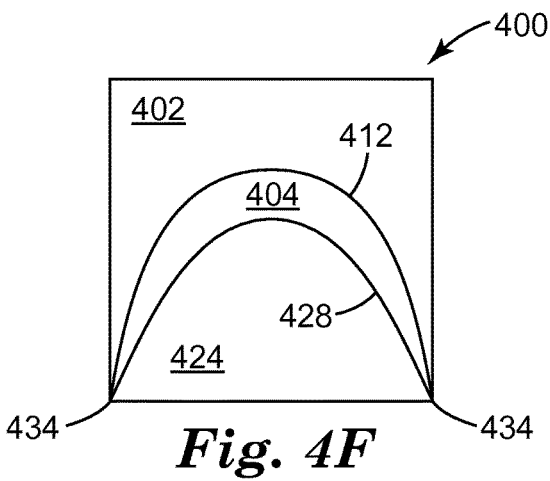

As illustrated in FIGS. 4A-4F, each of the first curve 412 and the second curve 438 has a different from zero curvature. FIGS. 4A and 4C provide examples of the first curve 412 and the second curve 428 having a greater than zero curvature in a semi-circular shape. FIG. 4C also provides an example where the first curve 412 and the second curve 428 are not symmetrical relative the second plane 418. FIGS. 4B, 4D and 4F provide examples of the first curve 412 and the second curve 438 both have a parabolic shape. FIG. 4F shows an example where the first curve 412 and the second curve 438 meet at a point 434, but do not cross. FIG. 4E provides an example of the first curve 412 having a parabolic shape and the second curve 428 having an oval shape. It is possible that at portion of the first curve 412 and/or the second curve 428 can be a straight line.

The dental mill blank of the present disclosure has been illustrated as a cuboid, as discussed herein. It is appreciated, however, that the surfaces defining the shape of the dental mill blank can have other shapes. For example, the faces of the dental mill blank can be configured to provide any one of the following shapes: cylindrical, prism (e.g., a uniform polyhedron with n-sided polygonal base or a non-uniform polyhedron with n-sided polygonal base), ovoid or conical shape, among others.

The dental mill blank of the present disclosure is a block (three dimensional article) of material from which a dental restoration can be machined. A dental mill blank may have a size suitable for the machining of one or more dental restorations.

The dental mill blank of the present disclosure can also include a mounting post or frame to facilitate affixation of the blank in a milling machine for milling a dental restorative. A mounting post or frame functions as handle by which a blank is held as it undergoes the milling process. An example of a device for such milling processes can include a CAM machine controlled by data provided by a CAD system (e.g., a CNC machine) for the shape of the desired dental restoration. Examples of such a computer-aided milling machine include those machines commercially available under the trade designations CEREC machine (available from Sirona Dental Systems, Bensheim, Germany) E4D (available from E4D Technologies, Richardson, Tex.), TS150 (available from IOS Technologies, San Diego, Calif.), LAVA (available from 3M ESPE, St. Paul, Minn.), DWX (available from Roland DGA, Irvine, Calif.), CS3000 (available from Carestream Health Inc., Atlanta, Ga.), CERAMILL (available from Amann Girrbach AG, Koblach, Austria), CERCON (available from Dentsply International, York, Pa.), RXD (available from Röders GmbH, Soltau, Germany), ZENOTEC (available from Weiland, Germany), EVEREST (available from KaVo Dental Corporation, Lake Zurich, Ill.), and PROCERA (available from Nobel Biocare USA, Inc., Westmont, Ill.), among others. U.S. Pat. Nos. 4,837,732 and 4,575,805 also disclose the technology of computer-aided milling machines for making dental prostheses. These machines produce dental prostheses by cutting, milling, and grinding the near-exact shape and morphology of a required restorative with greater speed and lower labor requirements than conventional hand-made procedures. By using a CAD/CAM milling device, the prosthesis can be fabricated efficiently and with precision. During milling, the contact area may be dry, or it may be flushed with or immersed in a lubricant. Alternatively, it may be flushed with an air or gas stream. Suitable liquid lubricants are well known, and include water, oils, glycerine, ethylene glycols, and silicones. Other machining process can include abrading, polishing, controlled vaporization, electronic discharge milling (EDM), cutting by water jet or laser or other method of cutting, removing, shaping or milling material. After milling, some degree of finishing, polishing and adjustment may be necessary to obtain a custom fit into the mouth and/or aesthetic appearance. Some ceramic or glass-ceramic materials might require one or more firing steps after milling. Once complete, one or more additional processing steps may be performed after the hardening step. Other processing steps may include trimming, polishing, coating, priming, staining, glazing, and the like.

A dental restoration can be prepared from the dental mill blank of the present disclosure. Examples of such dental restorations include, but are not limited to, those in the shape of a dental restorative, replacement, inlay, onlay, veneer, full crown, partial crown, bridge, denture, implant, implant abutment, implant healing cap, post, temporary restoration, and the like, or a part of any one of those dental restorations.

The method of preparing the dental restoration using the dental mill blank of the present disclosure can include designing the dental restoration with CAD/CAM software, as is known in the art. The dental mill blank of the present disclosure can be loaded into a milling machine, as discussed herein, and the design of the dental restoration can then be positioned within the dental mill blank. The dental restoration is then milled from the dental mill blank with the milling machine using the CAD/CAM software of the dental restoration. The dental restoration can then be polished and/or prepared for treating a patient. For example, a tooth structure of a patient can be treated with the dental restoration as prepared according to the present disclosure. In one example, treating the tooth structure can include attaching the dental restoration to the tooth structure with a dental cement, as are known in the art.

As discussed herein, natural teeth have color and translucency gradients from the gingival region to the incisal edge/occlusal surface. In an attempt to mimic these color and translucency gradients, dental mill blanks having multiple flat layers, with or without blended intermediate layers, or discrete shapes inside the mill blank have been suggested. However, positioning the restoration to achieve the desired outcome with the discrete shape blanks is perceived difficult by dentists, and transitions between flat layers are perceived to be unnatural.

The dental mill blank of the present disclosure, in contrast, reduces the difficulty in positioning the restoration design within the dental mill blank correctly. For example, as discussed herein, the dental mill blank includes both a first curve across the first plane of symmetry and the first straight line along the entire length of the second plane of the dental mill blank. As discussed, end points of this first straight line (or other straight lines when present) have the same relative position on the faces of the dental mill blank, opposite each other, on which they are present. The first straight line also maintains a parallel relationship with exterior edges of the dental mill blank. So, if the longitudinal axis (e.g., an axis of rotation) of the mounting post or frame is parallel with the first straight line in the dental mill blank, then the location of the dental restoration in the dental mill blank need only be positioned in the remaining two orthogonal planes (e.g., in the x-plane and the y-plane, as the first straight line, and any other straight lines, are in the z-plane of three-dimensional Cartesian coordinate system) to adjust for variations in the amount of enamel on the incisal edge of the dental restorative. This process is similar to that of dental restoratives produced with dental mill blanks having multiple flat layers.

So, positioning the dental mill blank of the present disclosure has the same convenience and simplicity of positioning the dental restorative in the dental mill blanks with multiple flat layers. But unlike dental mill blanks with multiple flat layers, the dental mill blanks of the present disclosure can produce dental restoratives that have gradients of shade and translucency with a more natural appearance. In addition, the dental mill blank of the present disclosure also eliminates the need for rotations and angle adjustments that are necessary for dental mill blank that contain discrete shapes, thus simplifying the positioning procedure for the restoration design within the dental mill blank while attaining better esthetic results.

In addition to simplifying the positioning the dental restorative in the dental mill blanks, producing the dental mill blank of the present disclosure can be done in a more cost effective matter than those that contain discrete shapes. For example, the dental mill blanks of the present disclosure can be produced in a continuous manner (e.g., a co-extrusion process), that leads to more cost effective production as compared to those dental mill blanks that are produced in a semi-continuous or a batch process (e.g., VITABLOCS® RealLife® (Vita Zahnfabrik H. Rauter GmbH & Co., Bad Säckingen, Germany; or CEREC® Blocks C In (Sirona Dental Technologies, Bensheim, Germany)).

As discussed herein, the dental mill blank of the present disclosure is composed of two or more layers having a difference in at least one of the shades and/or translucency of the hard restorative material that form the layers. The layers are shaped such that the color transition between layers appears gradual, even in the absence of physical blending between the layers. This visual blending allows for a more natural appearing color transition between the gingival and incisal/occlusal regions of the tooth as compared to dental mill blanks having only flat layers.

Figure 5:
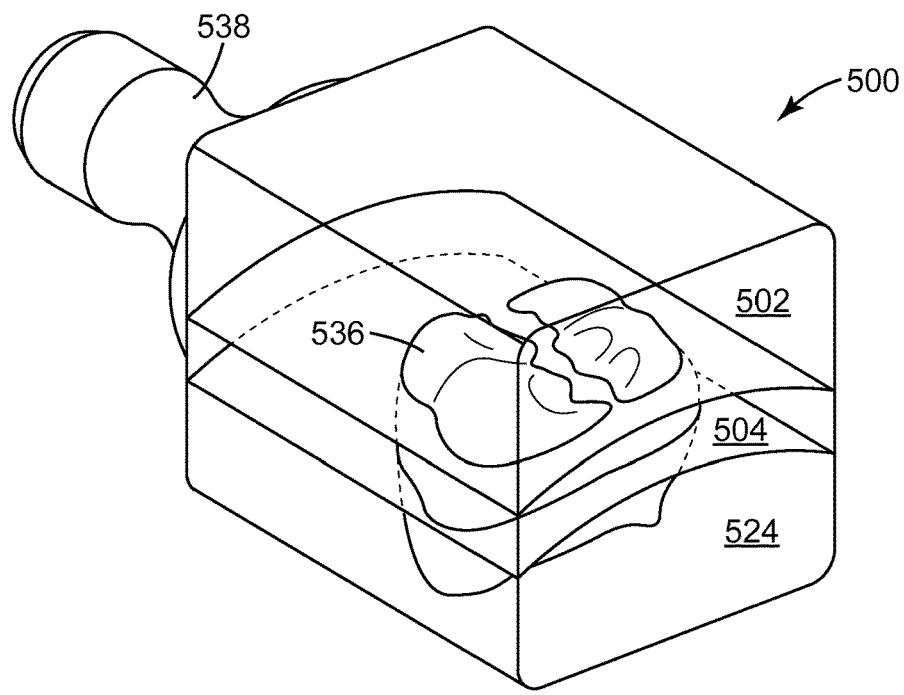
FIG. 5 is a perspective view of a dental mill blank according to an embodiment of the present disclosure.

Referring now to FIG. 5 there is shown an illustration of a dental mill blank 500 of the present disclosure having the outline of a dental restorative 536 (e.g., a crown) to be formed from the dental mill blank 500. As illustrated, the dental mill blank 500 includes three layers of the hard restorative material (e.g., the first layer 502, the second layer 504 and the third layer 524). Dental mill blank 500 is also shown having a mounting post 538.

As discussed herein, the first hard restorative material of the first layer 502 can have a translucency that is different from the translucency of the second hard restorative material of the second layer 504, and the translucency of the second hard restorative material of the second layer 504 can be different from the translucency of the third hard restorative material of the third layer 524. This and other combinations of differences in translucency and shade for the hard restorative materials used in forming the dental mill blank of the present disclosure allow for a more visually pleasing gradual transition for the color and shading of the dental restorative 536 by overlaying a more translucent layer over a darker layer. Simulating the dental restorative 536 placement in the dental mill blank shows that varying degrees of gradual transitions can be achieved when placing the crowns such that the buccal, facial and/or labial surfaces are oriented as shown in FIG. 5. It is recognized that the gradual transitions are on two faces of the block, so restorations need to be placed so that the visible (labial) surface is on the proper face of the block.

The purpose of the curved shape (e.g. parabolic, circular, etc.) for the interface between adjacent layers (e.g., the first layer and the second layer of the hard restorative material) having the described differences in the shade and/or the translucency of the hard restorative material is that during milling of a crown shape, portions of the exterior layer(s) (e.g., the first layer and possibly the second layer) will be gradually thinner towards the gingival margin of the crown. This thinning of the exterior layer(s) (e.g., the first layer of the hard restorative material) results in a gradual transition in color without the need for blending layers or incorporating intermediate layers due to the optical properties within the top layer. This will cause the boundaries between the layers to appear as gradual transitions.

In contrast to previously described methods of achieving a gradual transition in color, the approach described here uses sub-surface scattering properties of the hard restorative material and thickness variations of the layers to achieve the same goal. The advantage of the present disclosure is that the dental mill blank of the present disclosure containing the shaped layers is more easily produced than dental mill blanks with main and intermediate blended layers (such as Empress® Multi) or mill blanks containing discrete shapes (such as VITABLOCS® RealLife®, Vita Zahnfabrik H. Rauter GmbH & Co., Bad Säckingen, Germany; or CEREC® Blocks C In (Sirona Dental Technologies, Bensheim, Germany). Another aspect is that the placement of a crown inside the mill blank in preparation for milling is simpler than the placement in a mill blank with a discrete shape, as discussed herein.

Once formed, the milled dental restorative can be attached to the tooth or bone structure with conventional cements or adhesives or other appropriate means such as glass ionomer, resin cement, adhesive resin cement, self-adhesive resin cement, zinc phosphate, zinc polycarboxylate, compomer, or resin-modified glass ionomer. In addition, material can optionally be added to the milled dental restorative for various purposes including repair, correction, or enhancing esthetics. The additional material may be of one or more different shades or colors.

Examples of the restorative material that can be used in forming the hard restorative material of the various layers can include, but is not limited to, hardenable resins, thermoplastics, composites, ceramics, glasses, glass-ceramics, interpenetrating network materials, and combinations thereof, where these materials can undergo a physical and/or a chemical transformation to produce the hard restorative material. As provided herein, the hard restorative materials can be chosen from a group consisting of thermoplastic, composite, nanocomposite, ceramic, glass-ceramic, porcelain, lithium silicate glass-ceramic, lithium disilicate glass-ceramic and combinations thereof.

Examples of thermoplastics include, but are not limited to, those in the polyaryletherketone (PAEK) family, such as polyether ether ketone (PEEK); high molecular weight polyethylene (HMWPE); and acrylic polymers.

Examples of hardenable resins include, but are not limited to, those having sufficient strength, hydrolytic stability, and non-toxicity to render them suitable for use in the oral environment. Examples of such materials include acrylates, methacrylates, urethanes, carbamoylisocyanurates, epoxies (e.g., those shown in U.S. Pat. No. 3,066,112 (Bowen); U.S. Pat. No. 3,539,533 (Lee II et al.); U.S. Pat. No. 3,629,187 (Waller); U.S. Pat. No. 3,709,866 (Waller); U.S. Pat. No. 3,751,399 (Lee et al.); U.S. Pat. No. 3,766,132 (Lee et al.); U.S. Pat. No. 3,860,556 (Taylor); U.S. Pat. No. 4,002,669 (Gross et al.); U.S. Pat. No. 4,115,346 (Gross et al.); U.S. Pat. No. 4,259,117 (Yamauchi et al.); U.S. Pat. No. 4,292,029 (Craig et al.); U.S. Pat. No. 4,308,190 (Walkowiak et al.); U.S. Pat. No. 4,327,014 (Kawahara et al.); U.S. Pat. No. 4,379,695 (Orlowski et al.); U.S. Pat. No. 4,387,240 (Berg); U.S. Pat. No. 4,404,150 (Tsunekawa et al.)); and mixtures and derivatives thereof.

The hardenable resin may have free radically active functional groups and may include monomers, oligomers, and polymers. Suitable compounds contain at least one ethylenically unsaturated bond and can undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO 00/38619 (Guggenberger et al.), WO 01/92271 (Weinmann et al.), WO 01/07444 (Guggenberger et al.), WO 00/42092 (Guggenberger et al.) and fluoropolymer-functional (meth) acrylates as disclosed, for example, in U.S. Pat. Nos. 5,076,844 (Fock et al.) and 4,356,296 (Griffith et al.), EP 0373 384 (Wagenknecht et al.), EP 0201 031 (Reiners et al.), and EP 0201 778 (Reiners et al.). Mixtures of two or more free radically polymerizable compounds can be used if desired. In some embodiments, a methacryloyl-containing compound may be utilized.

The polymerizable component may also contain hydroxyl groups and ethylenically unsaturated groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from commercial sources, such as Sigma-Aldrich, St. Louis. Mixtures of ethylenically unsaturated compounds can be used.

In certain embodiments, the polymerizable resin includes a compound selected from the group consisting of dimethacrylates of polyethylene glycols of 200 to 1000 weight average molecular weight, such as PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), 4 to 10 mole ethoxylated Bisphenol-A dimethacrylate (Bis-EMA), such as bisEMA6 as described in U.S. Pat. No. 6,030,606 (Holmes), NPGDMA (neopentylglycol dimethacrylate), glycerol dimethacrylate, 1,3-propanediol dimethacrylate and 2-hydroxyethyl methacrylate. Various combinations of these hardenable components can be used. For certain embodiments, including any one of the above embodiments, the polymerizable resin comprises a compound selected from the group consisting of 2,2-bis[4-(2-hydroxy-3-methacryloyloxypropoxy)phenyl]propane (bisGMA), triethyleneglycol dimethacrylate (TEGDMA), urethane dimethacrylate (UDMA), 4 to 10 mole ethoxylated Bisphenol-A dimethacrylate (bisEMA), dimethacrylates of polyethylene glycols of 200 to 1000 weight average molecular weight, glycerol dimethacrylate, 1,3-propanediol dimethacrylate, and a combination thereof.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

In certain embodiments, one or more thermally activiated initiators is used to enable thermal curing of the resin component. Examples of thermal initiators include peroxides and azo compounds such as benzoyl peroxide, lauryl peroxide, 2,2-azobis-isobutyronitrile (AIBN).

In certain embodiments, the thermally activated initiator is chosen such that appreciable amounts of free-radical initiating species are not produced at temperatures below about 100° C. "Appreciable amounts" refers an amount sufficient to cause polymerization and/or crosslinking to the extent that a noticeable change in properties (e.g., viscosity, moldability, hardness, etc.) of the composition occurs. In addition, the temperature required for activation of the initiator to produce appreciable amounts of the free-radical initiating species does not exceed 150° C. For certain embodiments, the initiator is activated within the temperature range of 120 to 140° C., or, in some embodiments, 130 to 135° C. For certain of these embodiments, the initiator is an organic peroxide which can be thermally activated to produce appreciable amounts of free-radical initiating species within any of these temperature ranges. For certain of these embodiments, the initiator is selected from the group consisting of dicumyl peroxide, t-butyl peroxide, and a combination thereof. For certain of these embodiments, the initiator is dicumyl peroxide. In other embodiments, the initiator is selected from 2,5-Bis(tert-butylperoxy)-2,5-dimethylhexane; 2,5,-Bis(tert-Butylperoxy)-2,5-dimethyl-3-hexyne; Bis(1-(tert-butylperoxy)-1-methylethy)benzene; tert-butyl peracetate; tert-butyl peroxybenzoate; cumene hydroperoxide; 2,4-pentanedione peroxide; peracetic acid, and combinations thereof.

For certain embodiments, the thermally activated initiator is present in the composition in an amount of at least 0.2 percent based upon the weight of the polymerizable resin. For certain of these embodiments, the initiator is present in an amount of at least 0.5 percent. For certain of these embodiments, the initiator is present in the composition in the amount of not more than 3 percent based upon the weight of the polymerizable resin. For certain of these embodiments, the initiator is present in an amount of not more than 2 percent.

In certain embodiments, the composition may additionally be photopolymerizable, i.e., the composition contains a photoinitiator system that upon irradiation with actinic radiation initiates polymerization (curing or hardening) of the composition. Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. Nos. 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of different from 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

The phosphine oxide initiator may be used in the photopolymerizable composition in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the unfilled composition. Useful amounts of other initiators are well known to those of skill in the art.

Resins made from cationically curable material suitable for use in the present invention include epoxy resins. Epoxy resins impart high toughness to composites, a desirable feature for composite mill blanks Epoxy resins may optionally be blended with various combinations of polyols, methacrylates, acrylates, or vinyl ethers. Preferred epoxy resins include diglycidyl ether of bisphenol A (e.g. EPON 828, EPON 825; Shell Chemical Co.), 3,4-epoxycyclohexylmethyl-3-4-epoxy cyclohexene carboxylate (e.g. UVR-6105, Union Carbide), bisphenol F epoxides (e.g. GY-281; Ciba-Geigy), and polytetrahydrofuran.

As used herein, "cationically active functional groups" is a chemical moiety that is activated in the presence of an initiator capable of initiating cationic polymerization such that it is available for reaction with other compounds bearing cationically active functional groups. Materials having cationically active functional groups include cationically polymerizable epoxy resins. Such materials are organic compounds having an oxirane ring, i.e., a group of the formula

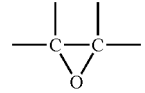

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar. Other types of useful materials having cationically active functional groups include vinyl ethers, oxetanes, spiro-orthocarbonates, spiro-orthoesters, and the like.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively, initiation systems for resins comprising cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. Pat. Nos. 6,025,406 and 5,998,549, each of which is incorporated herein by reference.

A filler for the composites of present invention is preferably a finely divided material that may optionally have an organic coating. Suitable coatings include silane or encapsulation in a polymeric matrix.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a cross-linked organic material that is insoluble in the polymerizable resin, and is optionally filled with inorganic filler. The filler should in any event be non-toxic and suitable for use in the mouth. The filler can be radiopaque, radiolucent or non-radiopaque. The filler may have any shape, including but not limited to equiaxed, spherical, polyhedral, oblong, lenticular, toroidall, whisker, or fiber.

Examples of suitable inorganic fillers are naturally-occurring or synthetic materials such as quartz, nitrides (e.g., silicon nitride); glasses containing, for example Ce, Sb, Sn, Zr, Sr, Ba, An, La, Y and Al; colloidal silica; feldspar; borosilicate glass; kaolin; talc; titania; and zinc glass; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.), non-vitreous microparticles of the type described in U.S. Pat. No. 4,503,169; non-pyrogenic nanoparticles of silica; nanoparticles of zirconia; and zirconia-silica fillers, including those in which the silica and zirconia nanoparticles are clumped together in the form of silica-zirconia nanoclusters.

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof. Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glasses have the added benefit of releasing fluoride at the site of dental work when placed in the oral environment.

Optionally, the surface of the filler particles may be treated with a surface treatment such as a coupling agent in order to enhance the bond between the filler and the polymerizable resin. The coupling agent may be functionalized with reactive curing groups, such as acrylates, methacrylates, epoxies, and the like. Examples of coupling agents include gamma-methacryloxypropyltrimethoxysilane, gamma-mercaptopropyltriethoxysilane, gamma-aminopropyltrimethoxysilane, beta-(3,4-epoxycyclohexyl)ethyl-trimethoxysilane, gamma-glycidoxypropyltrimethoxysilane, and the like.

In some embodiments, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses for certain embodiments may be preferred, since the glass typically contains sufficient elutable fluoride ions so that the thermally cured composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other components and will perform well when the resulting mixture is used in the mouth.

Generally, the average particle size (typically, diameter) for FAS glass used in such compositions is no different from about 12 micrometers, typically no different from 10 micrometers, and more typically no different from 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.).

Another class of useful filler are bioactive glasses and ceramics. Examples include BIOGLASS (U.S. Biomaterials; Alachua, Fla.); BIO-GRAN (Orthovia; Malvern, Pa.); CERABONE A-W (Nippon Electric Glass, Japan); NOVAMIN (GlaxoSmithKline); glasses comprising calcium oxide, silicon oxide, and phosphorous oxide; and the various phases of calcium phosphate including hydroxyapatite, monetite, brushite, and whitlockite.

The non-pyrogenic nanoparticles of silica and nanoparticles of zirconia may be prepared from dispersions, sols, or solutions of at least one precursor. Process of this nature are describe, for example, in U.S. Pat. No. 4,503,169 (Randklev) and GB Patent No. 2291053 B.

Zirconia-silica filler may be prepared from a silica sol and zirconyl acetate as described, for example, in U. S. Pat. No. 6,818,682 at column 11, line 40 through column 12, line 10. In another example, silica-zirconia nanocluster fillers may be prepared by mixing a nanosilica sol together with a preformed nanozirconia particulate sol. The nanozirconia sol is typically composed of crystalline zirconia nanoparticles. The use of a preformed nanozirconia sol, in certain circumstances, provides for silica-zirconia nanofillers with better opalescence properties than those derived from zirconyl acetate.

The silica sol typically comprises silica particles having a mean diameter from about 10 nm to about 100 nm, more typically from about 15 nm to about 60 nm, most typically from about 15 nm to about 35 nm, with a mean particle diameter of about 20 nm being particularly well-suited for fabrication of nanoclusters. The zirconia sol typically comprises zirconia particles that are small enough to not scatter the majority of visible light, but are large enough to refract shorter wavelength blue light to give the opalescent effect. A zirconia sol having a mean particle size from about 3 nm to about 30 nm is suitable for forming the nanoclusters. Typically, the zirconia particles in the sol have a mean particle diameter from about 5 nm to about 15 nm, more typically from about 6 nm to about 12 nm, and most typically from about 7 nm to about 10 nm. When mixed together under acidic conditions where the sol mixture is stable, such as at a pH of below 2, the preformed zirconia nanoparticles form a structure with the silica nanoparticles on gelling and drying that gives the desired opalescence character while maintaining a high level of optical transparency of the final composite material.

NALCO 1042 silica sol (Nalco Chemical Company, Naperville, Ill.) or other commercially available colloidal silica sols may be used. If a base-stabilized sol is used, typically it will first be subjected to ion exchange in order to remove sodium, for example, with an AMBERLITE IR-120 ion exchange resin, or pH adjusted with nitric acid. It is usually desirable to pH adjust the silica to below 1.2, typically about 0.8 to about 1.0, and then add the zirconia to it slowly, to prevent localized gelation and agglomeration. The pH of the resultant mixture is typically about 1.1 to about 1.2. Suitable colloidal silica sols are available from a variety of vendors, including Nalco (Ondeo-Nalco, Grace chemical), H. C. Stark, Nissan Chemical (Snowtex), Nyacol, and Ludox (DuPont). The selected sol should have silica particles that are discrete and of the appropriate size specified herein. The silica sol may be treated to provide a highly acidic silica sol (e.g., nitrate stabilized) that can be mixed with the zirconia sol without gelation.

The zirconia sol may be obtained using a process described, for example, in U.S. Pat. No. 6,376,590 (Kolb, et al.), or U.S. Pat. No. 7,429,422 (Davidson et al.) the disclosures of which are incorporated by reference herein. As used herein, the term "zirconia" refers to various stoichiometries for zirconium oxides, most typically $ZrO_2$, and may also be known as zirconium oxide or zirconium dioxide. The zirconia may contain up to 30 weight percent of other chemical moieties such as, for example, $Y_2O_3$ and organic material.

The silica-zirconia nanoclusters can be prepared by mixing together the nanosilica sol with the nanozirconia sol, and heating the mixture to at least 450° C. Typically, the mixture is heated for 4 to 24 hours at a temperature between about 400 to about 1000° C., more typically from about 450 to about 950° C., to remove water, organic materials, and other volatile components, as well as to potentially weakly aggregate the particles (not required). Alternatively, or in addition, the sol mixture may undergo a different processing step to remove water and volatiles. The resulting material may be milled or ground and classified to remove large aggregates. The filler may then be surface treated with, for example, a silane prior to mixing with a resin.

Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); U.S. Pat. No. 7,022,173 (Cummings et al); U.S. Pat. No. 6,306,926 (Bretscher et al); U.S. Pat. No. 7,030,049 (Rusin et al); U.S. Pat. No. 7,160,528 (Rusin); U.S. Pat. No. 7,393,882 (Wu et al); U.S. Pat. No. 6,730,156 (Windisch et al); U.S. Pat. No. 6,387,981 (Zhang et al); U.S. Pat. No. 7,090,722 (Budd et al); U.S. Pat. No. 7,156,911 (Kangas et al); U.S. Pat. No. 7,361,216 (Kolb et al); as well as in International Publication No. WO 03/063804 (Wu et al.), incorporated herein by reference. Filler components described in these references include nanosized silica particles, nanosized metal oxide particles, and combinations thereof. Nanofillers are also described in U.S. Pat. No. 7,085,063 (Kangas et al.); U.S. Pat. No. 7,090,721 (Craig et al.) and U.S. Pat. No. 7,649,029 (Kolb et al.); and U.S. Patent Publication Nos. 2010/0089286 (Craig et al); US 2011/0196062 (Craig et al);, all incorporated herein by reference.

Additional examples of composite compositions suitable for use in dental CAD/CAM include but are not limited to those described in U.S. Pat. No. 7,845,947 (Rusin et al); U.S. Pat. No. 6,345,984 (Karmaker et al); U.S. Pat. No. 6,846,181 (Karmaker et al); U.S. Pat. No. 5,990,195 (Arita); as well as in U.S. Patent Publication Nos. 2013/172441 (Takehata et al); 2009/220917 (Jensen); 2009/220918 (Jensen); incorporated herein by reference. Other examples of composite compositions are those described in International Publication No. WO 2011/087832 (Craig et al), incorporated herein by reference.

In some embodiments, hardenable resin is unfilled; this may be suitable, for example, for temporary restorations, or demonstration materials. In other embodiments, filler is present in an amount sufficient to impart desired properties such as mechanical strength and toughness, wear resistance, esthetics, and other characteristics. Wear resistance, in particular, is highly dependent upon the filler loading, especially as the percolation threshold (maximum loading) is approached for a filler.

The compositions and mill blanks provided herein may optionally comprise additives suitable for use in the oral environment, including colorants, agents that impart fluorescence and/or opalescence, dyes (including photobleachable dyes), pigments, flavorants, indicators, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Other materials suitable for producing the dental mill blank of the present disclosure can include those used to form various commercially available dental mill blanks Examples of such commercially available dental mill blanks include, but are not limited to, MARK II, ENAMIC, CAD TEMP, IN-CERAM, YZ, and CEREC BLOCKS (available from Vita Zahnfabrik, Germany), EMPRESS CAD, E.MAX CAD, and TELIO CAD (available from Ivoclar Vivadent, Lichtenstein), PARADIGM MZ100, PARADIGM C, LAVA ULTIMATE, LAVA ZIRCONIA, LAVA FRAME, LAVA PLUS (available from 3M ESPE, St. Paul, Minn.), AMBARINO HIGH GLASS (available from Creamed, Germany), other suitable dental materials, or combinations thereof.

Examples of ceramics include but are not limited to zirconia, alumina, magnesium aluminate spinel, and mixtures thereof. Examples of these materials are described in U.S. Pat. No. 6,878,456 (Castro et al); U.S. Pat. No. 6,713,421 (Hauptmann et al); and U.S. Pat. No. 8,309,015 (Rolf et al).

Examples of glass-ceramics include but are not limited to dental porcelains, feldspathic glass-ceramics, potassia-alumina-silica glass-ceramics, and nepheline glass-ceramics.

Another useful family of materials is lithium silicate glass-ceramics. Examples of these materials are described in U.S. Pat. No. 8,536,078 (Ritzberger et al); U.S. Pat. No. 6,342,458 (Schweiger et al); U.S. Pat. No. 7,993,137 (Apel et al); U.S. Pat. No. 7,892,995 (Castillo); and in U.S. Patent Publication No. 2011/0257000 (Ritzberger et al);

Another useful family of materials is alumina glasses and glass-ceramics. Examples of these materials are described in U.S. Pat. No. 6,984,261 (Cummings et al).

Other useful families of materials are mica glass-ceramics, for example those described in U.S. Pat. No. 6,375,729 (Brodkin et al); cordierite glass-ceramics, for example those described in U.S. Pat. No. 4,957,554 (Mathers et al); lanthana glass-ceramics, for example those described in U.S. Pat. No. 8,133,828 (Denry et al); and rare earth glass-ceramics, for example those described in U.S. Pat. No. 7,160,528 (Rusin).

Another useful family of materials is interpenetrating network composites (IPN), wherein a porous glass, glass-ceramic, or ceramic network is infiltrated with a hardenable resin or molten glass to form a solid body. Examples of IPN materials using a hardenable resin infiltrant are described in U.S. Pat. No. 5,869,548 (Ikushima et al); 8,507,578 (Sadoun); U.S. Pat. No. 6,159,417 (Giordano et al); U.S. Pat. No. 6,271,282 (Giordano); U.S. Pat. No. 6,881,488 (Giordano); and in U.S. Patent Publication Nos. 2013/115364 (Zandinejad); 2004/024470 (Giordano); 2004/081847 (Aechtner et al). Examples of IPN materials using a glass infiltrant are described in U.S. Pat. No. 4,772,436 (Tyszblat); U.S. Pat. No. 5,910,273 (Thiel).

The method of forming the dental blank of the present disclosure can include joining a first layer of a first restorative material and a second layer of a second restorative material to form the first interface and the smooth curve for the first interface, as discussed herein. The first restorative material and the second restorative material are then hardened or fired to form the first hard restorative material having the first translucency and the first shade, and the second hard restorative material having the second translucency and the second shade, as provided herein. The method can further include joining a third layer of a third restorative material with the second layer of the second restorative material, where the second layer and the third layer form a second interface having the second curve across the first plane of symmetry of the dental mill blank, as discussed herein. The third restorative material can be hardened or fired along with the first restorative material and the second restorative material to form the first hard restorative material, the second hard restorative material and a third hard restorative material of the dental mill blank.

One approach to joining the first layer of the first restorative material and the second layer of a second restorative material is through an extrusion process. For example, the first restorative material and the second restorative material can be co-extruded through one or more dies, having the appropriate cross-sectional profile, to make physical contact at the first interface. Similarly, the third restorative material can be co-extruded through one or more dies with the first restorative material and the second restorative material to make physical contact between the first restorative material and the second restorative material at the first interface and between the second restorative material and the third restorative material at the second interface. The extrusion process can be a continuous process or a semi-continuous process, as desired.

Co-extrusion is the process of extruding two or more materials through a single die with two or more orifices arranged so that the extrudates merge and weld together into a laminar structure before being hardened as discussed herein. Each material is fed to the die from a separate extruder, but the orifices may be arranged so that each extruder supplies two or more plies of the same material. Various methods for coextruding two or more pastes to form a single layered structure are known in the art, as described for example in Polymer Rheology (R. S. Lenk, 1978, Springer Netherlands, ISBN: 978-94-010-9668-3); Extrusion Coating, Lamination and Coextrusion: The complete process manual (B. H. Gregory, 2012, Plastics Information Direct (UK) , ISBN-13: 978-1906479084); Engineered Materials Handbook Volume 2: Engineering Plastics (1988 ASM International, ISBN 0-87170-279-7).

Another approach to joining the first layer of the first restorative material and the second layer of a second restorative material is through an extrusion process in which each individual layer is sequentially extruded into a mold. For example, other approaches to joining the first layer of the first restorative material and the second layer of a second restorative material (or more layers) is through calendaring, shot forming, or injection molding.

For glass, ceramic, or glass-ceramic materials, the various processes described above may be done using a slip, slurry, or paste of the glass, ceramic, or glass-ceramic. The slip, slurry, or paste may have a medium or carrier along with other modifiers and adjuvants known in the art. After forming, the slip, slurry, or paste may be subjected to one or more additional steps including but not limited to drying, burnout of organics, firing, sintering, hot pressing, and the like.

Layers of glass or glass-ceramic materials may be formed in the molten state via various extrusion or hot pressing processes known in the art.

Other approaches to forming the layered blanks include sequential pressing, injection molding, and/or additive buildup techniques. Additive buildup techniques include selective laser sintering, three-dimensional printing, stereolithography (SLA), or deposition of a suspension of the component materials.

Dental mill blanks of the present disclosure may be subjected to further processing steps including but not limited to trimming, surface finishing, printing, and the like. Indicia such as bar codes, QR codes, or other may be printed or embossed on the blank surface. Optionally, the dental mill blanks of the present disclosure may further include a holder. For example, the dental mill blanks of the present disclosure may be mounted on a holder. Examples of such holders include but are not limited to a frame, a stub, a mandrel, a post, and the like.

The restorative materials are then hardened to form the hard restorative materials discussed herein (e.g., the hard first restorative material, the hard second restorative material and, optionally, the hard third restorative material). Hardening the restorative materials can be accomplished based on the type of restorative material used.

For example, the restorative material can be hardened, when appropriate, using heat, light, microwave, e-beam, fusing, sintering, firing or chemical cure. Once hardened, the dental mill blank of the present disclosure can be trimmed if necessary; and optionally, mounted on a holder stub or post if necessary.

Figure 10:
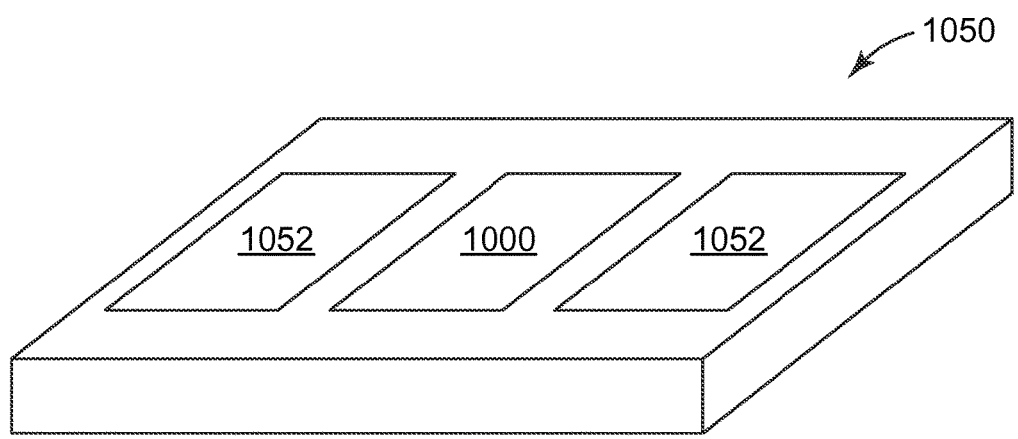
FIG. 10 is an illustration of a kit that includes the dental mill blank of the present disclosure.

Referring now to FIG. 10, there is shown a kit 1050 according to the present disclosure. The kit 1050 includes the dental mill blank 1000 discussed herein. In addition to the dental mill blank 1000, the kit 1050 can include at least one dental component 1052 selected from the group of a cement, an adhesive, an abrasive, a polishing paste, an instrument, software, a mill, a CAD/CAM system, a composite, a porcelain, a stain, a bur, an impression material, a mill block or a combination thereof. As discussed herein, the dental mill blank 1000 in the kit 1050 can be fixed to a mounting post or a frame.

EXAMPLES

Objects and advantages of this disclosure are further illustrated by the following examples, but the particular materials and amounts thereof recited in these examples, as well as other conditions and details, should not be construed to unduly limit this disclosure. Unless otherwise indicated, all parts and percentages are by weight and all molecular weights are weight average molecular weight.

Color Characterization: CIELAB and Dental Shades

Color is characterized via CIELAB values measured with a spectrophotometer, or by a color (or shade) system common in the dental industry. Examples of such dental color systems are the Vitapan™ Classical and Vita 3D Master™, both from VITA Zahnfabrik H. Rauter GmbH & Co. KG, and Chromascop™ from Ivoclar Vivadent AG. The CIELAB color system (also known as CIE 1976 (L*, a*, b*) color space) has been defined by the Commission Internationale De l'Eclairage.

Method for Measuring Contrast Ratio 1.0 millimeter (mm) thick tiles sectioned from the blanks were polished with 600 grit sandpaper. Tristimulus color values were measured against white and black backgrounds on an X-Rite™ Color i7 spectrophotometer. The contrast ratio, C, is calculated as the ratio of the Y-tristimulus value of a material on a black substrate to that on a white substrate. Thus $C=Y_B/Y_W$, where $Y_B$ is the reflectance of a ceramic wafer on a black substrate and $Y_W$ is the reflectance of the same wafer on a white substrate. This technique is based on Section 3.2.1 of ASTM D2805-95 "Standard Test Method for Hiding Power of Paints by Reflectometry", modified for 1 mm thick samples. The lower the contrast ratio, the more translucent the material.

Method for Measuring Color 1.0 mm thick tiles sectioned from the blanks were polished with 600 grit sandpaper. CIELAB color coordinates were measured against white background on an X-Rite™ Color i7 spectrophotometer.

Preparation and Curing of Pastes

A polymerizable resin was prepared according to Table 1 in WO 2011/087832 (Craig et al.), with the addition of 1% dicumyl peroxide. Dental fillers described in WO 2011/087832 were compounded with the polymerizable resin into a paste, in the amounts shown in Table 1, below. Also included were small levels of pigments to attain various shades in the Vitapan Classical system, and also different translucency levels. Shades with the designation LT have a contrast ratio approximately 60.5, and HT approximately 53.5.

TABLE 1

Paste Composition

| Component | Amount (weight %) |
| --- | --- |
| Polymerizable resin | 20.5 |
| ST Nanozirconia | 4.17 |
| ST 20 nm Silica | 7.75 |
| ST Silica/Ziconia Clusters | 67.58 |

Pastes of two or three different shades and/or translucencies were coextruded to form layers with curved interfaces. The extruded pastes were cured according to conditions described in WO 2011/087832 (Craig et al.) under "Example: formation of a net shape crown by molding".

Example 1

Figure 6:
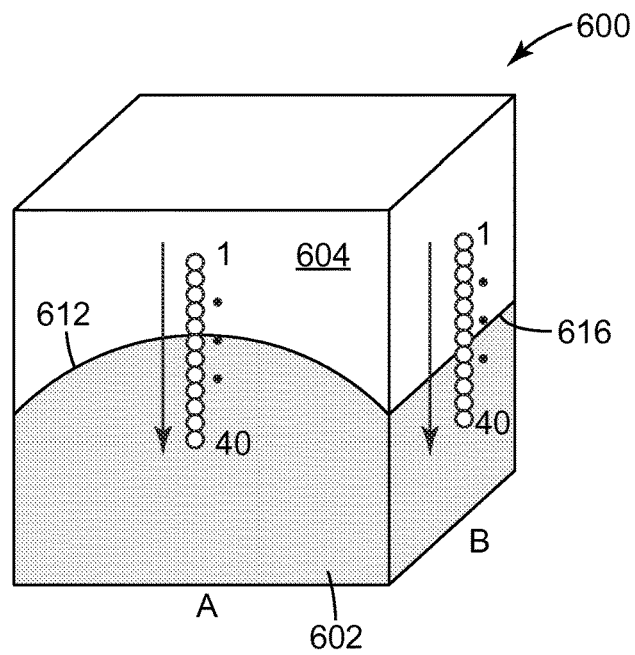
FIG. 6 is a drawing of a dental mill blank according to Example 1 of the present disclosure, where locations of relative measurement for the brightness (L*) and blue-yellow (b*) transitions data (shown in FIGS. 7A and 7B) are shown along the surfaces of the dental mill blank.

The dental mill blank 600 of Example 1, illustrated in FIG. 6, is approximately 14 mm×14 mm×18 mm. The dental mill blank 600 is formed with a first layer 602 of a first hard restorative material having a A3-LT shade (A3) and translucency (low translucency) and a second layer 604 of a second hard restorative material having a A2-HT shade (A2) and translucency (high translucency). Table 2 provides the L*, a*, b* and contrast ratio (CR) values for the layers 602 and 604.

TABLE 2

| Name | L* | a* | b* | CR |
|---|---|---|---|---|
| Second Layer A2-HT | 84 | 1.25 | 18.5 | 53.4 |
| First Layer A3-LT | 81.5 | 2.5 | 23 | 60.5 |

The two layers were formed from the paste and coextruded, both as discussed above. The coextruded dental mill blank of Example 1 was cured according to conditions described in WO 2011/087832 (Craig et al.) under "Example: formation of a net shape crown by molding". The interface of the first layer and the second layer each form a first curve 612 having the shape of a circular arc having a radius of 10 mm across the first plane of symmetry of the dental mill blank, and also provide a first straight line 616 along the entire length of a second plane of the dental mill blank of Example 1.

Figure 7A:
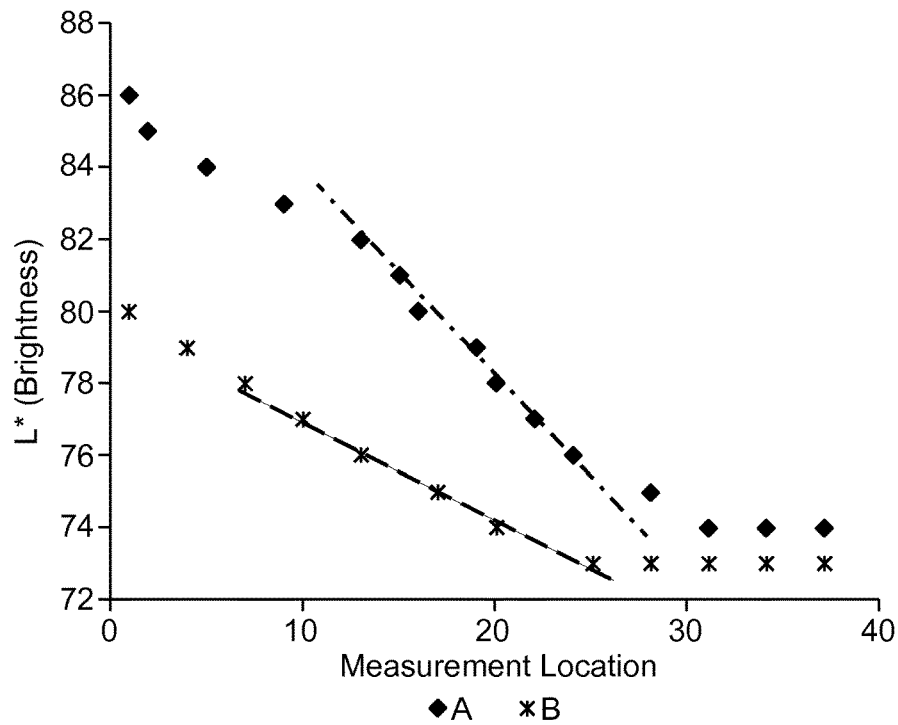
FIGS. 7A and 7B are graphs showing the brightness (L*) and blue-yellow (b*) transitions in surfaces of the dental mill blank of Example 1.
Figure 7B:
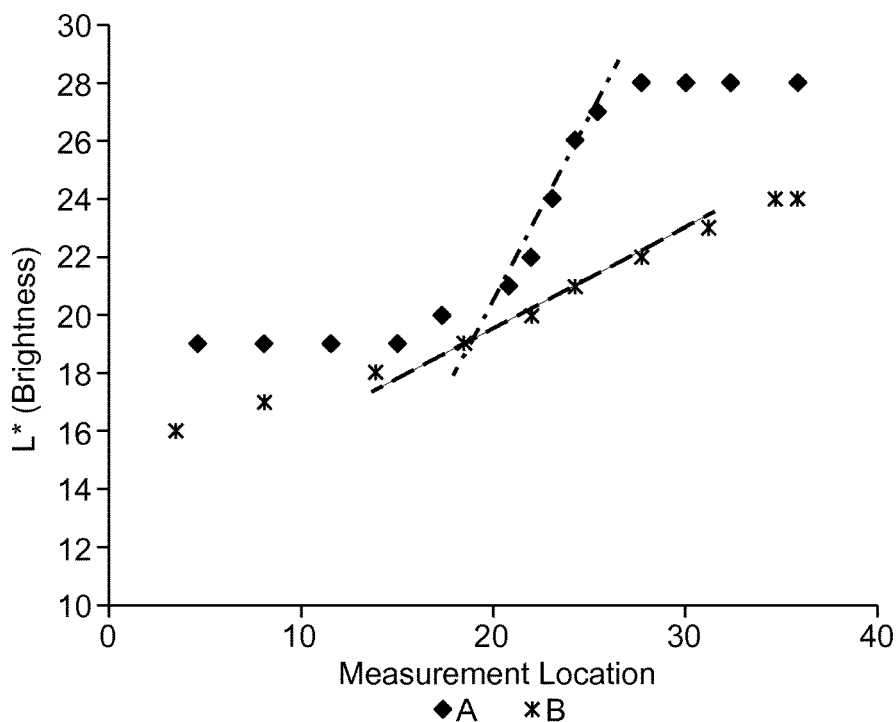

FIGS. 7A and 7B show the L* and b* transitions in the dental mill blank 600 of Example 1 shown in FIG. 6. The L* and b* transitions were obtained from by photographing a white matte background in a photo-setup utilizing evenly scattering illumination. An image of Netprofiler™ Benchtop Standard BTS183C color tiles from X-Rite and images of the planar surfaces A and B of the dental mill blank 600 of Example 1 were taken in the same setup using the same camera and settings. The standard color tiles were then measured on an X-Rite Spectrophotometer model Color i7 to obtain L*a*b* values. The white image was used to correct the CCD (charge-coupled device) array of the camera for flat field errors and then generate a flat image field in Adobe Photoshop. Next, an Adobe Photoshop macro for color correction was generated by correcting each color tile image to agree with the L*a*b* value measured on the Spectrophotometer. The field flattening and color correction macros were then run on each of the images of the dental mill blank 600 of Example 1. After correcting the images, a line of small circles was drawn perpendicular to the direction of the layers (as seen in FIG. 6) to mark the measurement locations. L*a*b* values in each circle were read and recorded.

As seen in FIGS. 7A and 7B, the transition zone for both L* and b* is shorter and steeper for measurement direction A than for measurement direction B indicating a more gradual change in brightness and color when the second layer 604 layer gradually thins toward the surface, which allows the first layer 602 to gradually show through the second layer 604. The transition along measurement direction A also shows a slight gradient instead of an expected step change, which is caused by subsurface scattering properties of the material.

Example 2

Figure 8:
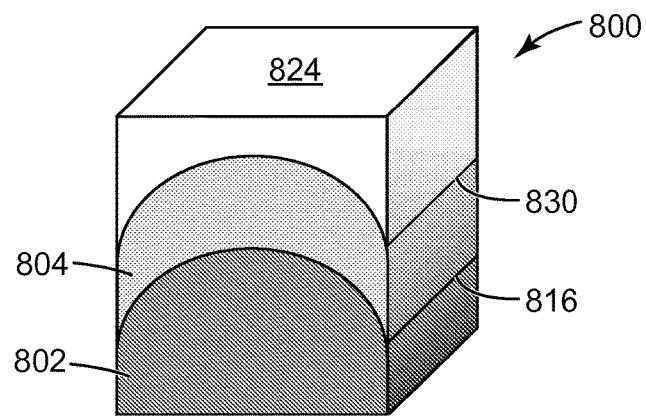
FIG. 8 is a drawing of a dental mill blank according to Example 2 of the present disclosure.

To demonstrate the more natural appearance of a dental restorative milled from the dental mill blank of the present disclosure, a first anterior crown was milled out of a dental mill blank 800 of FIG. 8 and a second anterior crown, identical to the first anterior crown, was milled out of a monolithic Lava™ Ultimate™ A2HT CAD/CAM Restorative mill blank.

The dental mill blank 800 of FIG. 8 is approximately 14 mm×14 mm×18 mm. The dental mill blank 800 is formed with a first layer 802 of a first hard restorative material having a A3-LT shade (A3) and translucency (low translucency), a second layer 804 of a second hard restorative material having a A2-LT shade (A2) and translucency (low translucency), and a third layer 824 of a third hard restorative material having a A1-HT shade (A1) and translucency (high translucency). Table 3 provides the L*, a*, b* and contrast ratio (CR) values for the layers 802, 804 and 824.

TABLE 3

|  | L* | a* | b* | CR |
|---|---|---|---|---|
| Third Layer A1-HT | 87 | −1 | 10 | 53.4 |
| Second Layer A2-LT | 84 | 1.25 | 18.5 | 60.5 |
| First Layer A3-LT | 81.5 | 2.5 | 23 | 60.5 |

The three layers were formed from the paste and coextruded, both as discussed above. The coextruded dental mill blank 800 used in Example 2 was cured according to conditions described in WO 2011/087832 (Craig et al.) under "Example: formation of a net shape crown by molding". The first interface (e.g. the interface of the first layer and the second layer) and the second interface (e.g., the interface of the second layer and the third layer) each form a parabolic arc across the first plane of symmetry of the dental mill blank, and also provide a first straight line 816 and a second straight line 830 along the entire length of a second plane of the dental mill blank 800 used in Example 2.

The crowns were milled using a Cerec MCXL Chairside CAD/CAM machine from Sirona (Germany). After milling, the crowns were polished with Diamond Twist SCL™ diamond paste from Premier and a bristle brush in a dental handpiece (model Ultimate XL-K) from NSK.

Figure 9A:
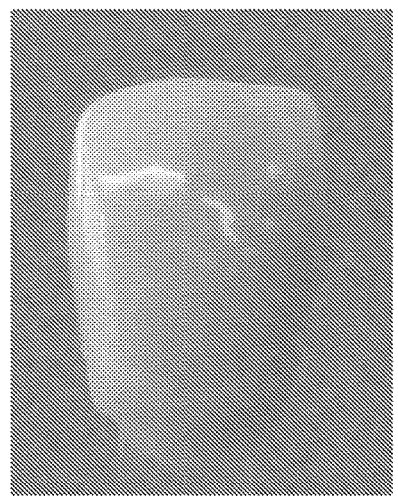
FIGS. 9A and 9B are photographs of dental crowns milled from the dental mill blank of Example 2 and a monolithic Lava™ Ultimate™ A2HT CAD/CAM Restorative mill blank.
Figure 9B:
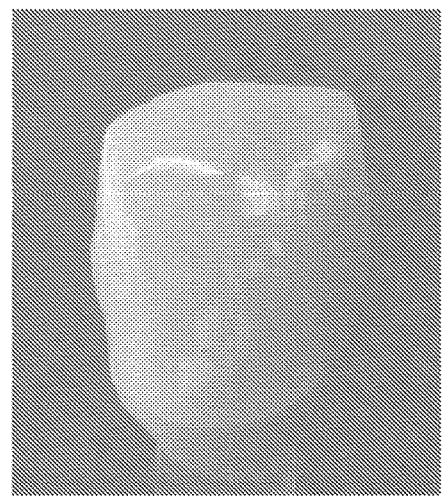

FIGS. 9A and 9B are photographs showing the crown milled from the dental mill blank 800 of FIG. 8 (FIG. 9A) and the crown milled from the monolithic dental mill blank (FIG. 9B). The crown milled from the dental mill blank 800 of Example 8 (FIG. 9A) shows a gradual transition from slightly darker less translucent shade at the gingival margin of the crown to more translucent, lighter shaded incisal edge. The crown milled from the monolithic dental mill blank (FIG. 9B) shows a very slight transition from the margin to the incisal edge variation due to the varying wall thickness of the restoration and resulting translucency of the material used for the restoration, but no shade transition.

Example 3

Milling Time of Anterior Crown Using Dental Mill Blank of Example 2

A first anterior crown was milled from a dental mill blank 800 formed according to Example 2 on a CEREC MCXL from Sirona (Germany). After loading the dental mill blank 800 in the CEREC MCXL the dental restoration was milled according to the CAD software option for a VITABLOCS® RealLife® discrete internal shape dental mill blank.

A second anterior crown, identical to the first anterior crown, was also milled from a dental mill blank 800 formed according to Example 2 on a CEREC MCXL from Sirona (Germany). After loading the dental mill blank 800 in the CEREC MCXL the dental restoration was milled according to the CAD software option for a VITABLOCS® TriLuxe dental mill blank (a flat layered multishade dental mill blank).

The time from start to completion of the milling cycle for both the first anterior crown and the second anterior crown were measured with a stopwatch. The milling times for the first anterior crown and the second anterior crown are shown in Table 4.

TABLE 4

| CAD Software Option used in Milling Dental Mill Blank of Example 2 | RealLife | TriLuxe |
| --- | --- | --- |
| Milling Time (minutes:seconds) | 23:55 | 15:54 |

It is believed that the second anterior crown will be as aesthetically pleasing as a crown milled from a VITABLOCS® RealLife® discrete internal shape dental mill blank, but as illustrated in Table 4 will possibly be produced in a fraction of the time (e.g., about 30 percent faster).

We claim:

1. A dental mill blank, comprising:
a first layer of a first hard restorative material having a first translucency and a first shade; and
a second layer of a second hard restorative material having a second translucency and a second shade;
where the first layer and the second layer form a first interface having:
a first curve across a first plane of symmetry of the dental mill blank, where the first curve has a different from zero curvature; and
a first straight line along the entire length of a second plane that passes through both the first layer and the second layer of the dental mill blank, the first straight line extending along the entire length of the dental mill blank and having end points that have the same relative positions on opposing faces of the dental block, the second plane being orthogonal to the first plane of symmetry; and
where at least one of the following is true:
the first translucency is different from the second translucency and
the first shade is different from the second shade.

2. The dental mill blank of claim 1, where the first curve is selected from the group consisting of a circle, a semicircle, a circular arc, an ellipse, an ellipsoidal arc, a parabola, an oval, a semi-oval, an ovoid arc and a catenary.

3. The dental mill blank of claim 1, where the second plane is a plane of symmetry for the dental mill blank.

4. The dental mill blank of claim 1, where the first layer of the first hard restorative material has a negative curvature and the second layer of the second hard restorative material has a positive curvature.

5. The dental mill blank of claim 1, where the first translucency is different from the second translucency.

6. The dental mill blank of claim 5, where the first shade and the second shade are equal.

7. The dental mill blank of claim 5, where the first shade is different from the second shade.

8. The dental mill blank of claim 1, where the first hard restorative material and the second hard restorative material are not physically blended at the first interface.

9. The dental mill blank of claim 1, further including a third layer of a third hard restorative material, where the third layer and the second layer form a second interface.

10. The dental mill blank of claim 9, where the third hard restorative material has a third translucency and a third shade, where at least one of the following is true:
the second translucency is different from the third translucency; and
the second shade is different from the third shade.

11. The dental mill blank of claim 9, where the second layer and the third layer form a second interface having:
a second curve across the first plane of symmetry of the dental mill blank, where the second curve has a different from zero curvature; and
a second straight line along the entire length of the second plane of the dental mill blank, the second plane being orthogonal to the first plane of symmetry.

12. The dental mill blank according to claim 1, wherein the dental mill blank is a cuboid having six quadrilateral faces.

13. The dental mill blank according to claim 12, wherein the dental mill blank is a cube, a rectangle cuboid, or a tetragonal prism.

14. A dental restoration shaped from the dental mill blank of claim 1.

15. The dental restoration of claim 14, where the dental restoration has the shape of a dental inlay, onlay, veneer, full crown, partial crown, bridge, denture, implant, implant abutment, implant healing cap, post, temporary restoration or a part of any one of those dental restorations.

16. A method of forming a dental mill blank, comprising:
joining a first layer of a first restorative material and a second layer of a second restorative material to form a first interface having:
a first curve across a first plane of symmetry of the dental mill blank, where the first curve has a different from zero curvature; and
a first straight line along the entire length of a second plane of the dental mill blank, the second plane being orthogonal to the first plane of symmetry; and
hardening the first restorative material and the second restorative material to form a first hard restorative material having a first translucency and a first shade, and a second hard restorative material having a second translucency and a second shade, where at least one of the following is true:
the first translucency is different from the second translucency; and
the first shade is different from the second shade.

17. The method of claim 16, where joining the first layer of the first restorative material and the second layer of the second hard restorative material forms a smooth curve for the first interface.

18. The method of claim 16, where joining the first layer of the first restorative material and the second layer of the second hard restorative material forms a plane of symmetry for the second plane of the dental mill blank.

19. The method of claim 16, further including joining a third layer of a third restorative material with the second layer of the second restorative material, where the second layer and the third layer form a second interface having:
a second curve across the first plane of symmetry of the dental mill blank, where the second curve has a different from zero curvature; and
a second straight line across the entire length of the second plane of the dental mill blank, the second plane being orthogonal to the first plane of symmetry; and
hardening the third restorative material along with the first restorative material and the second restorative material to form the first hard restorative material, the second hard restorative material and a third hard restorative material of the dental mill blank.

20. The method of claim 19, where the third hard restorative material has a third translucency and a third shade, where at least one of the following is true:

the second translucency is different from the third translucency; and the second shade is different from the third shade.

21. A method of preparing a dental restoration, comprising:

designing the dental restoration with CAD/CAM software;

positioning the restoration within a dental mill blank of claim 1; and milling the dental restoration from the dental mill blank with a milling machine using the CAD/CAM software of the dental restoration.

\* \* \* \* \*

UNITED STATES PATENT AND TRADEMARK OFFICE
CERTIFICATE OF CORRECTION

PATENT NO. : 10,219,880 B2
APPLICATION NO. : 15/026293
DATED : March 5, 2019
INVENTOR(S) : Rolf et al.

Page 1 of 1

It is certified that error appears in the above-identified patent and that said Letters Patent is hereby corrected as shown below:

On the Title Page

Column 2
Item (57), (Abstract), Line 1, after "herein" insert -- is --.

In the Specification

Column 14
Lines 12-13, delete "2-hydroxethyl" and insert -- 2-hydroxyethyl --, therefor.

Column 14
Line 35, delete "activiated" and insert -- activated --, therefor.

Column 17
Line 67, delete "toroidall," and insert -- toroidal, --, therefor.

Column 20
Line 46, delete "al);," and insert -- al.); --, therefor.

Column 21
Line 31, after "blanks" insert -- . --.

Column 21
Line 56, delete "al);" and insert -- al). --, therefor.

Column 24
Line 49 (approx.), delete "/Ziconia" and insert -- /Zirconia --, therefor.

Signed and Sealed this
Twenty-ninth Day of October, 2019

Andrei Iancu
*Director of the United States Patent and Trademark Office*